(12) United States Patent
Zhu

(10) Patent No.: US 11,013,532 B2
(45) Date of Patent: May 25, 2021

(54) TROCAR SEAL MEMBRANE WITH CONCAVE-CHANNEL STRUCTURE

(71) Applicant: 5RMED TECHNOLOGY(CHENGDU) CO., LTD., Chengdu (CN)

(72) Inventor: Moshu Zhu, Chengdu (CN)

(*) Notice: Subject to any disclaimer, the term of this patent is extended or adjusted under 35 U.S.C. 154(b) by 188 days.

(21) Appl. No.: 16/249,896

(22) Filed: Jan. 17, 2019

(65) Prior Publication Data
US 2019/0142459 A1 May 16, 2019

Related U.S. Application Data

(63) Continuation of application No. PCT/CN2017/093602, filed on Jul. 20, 2017.

(51) Int. Cl.
*A61B 17/34* (2006.01)
*A61B 17/00* (2006.01)
*A61M 39/06* (2006.01)

(52) U.S. Cl.
CPC .......... *A61B 17/3439* (2013.01); *A61B 17/00* (2013.01); *A61B 17/34* (2013.01);
(Continued)

(58) Field of Classification Search
CPC .............. A61B 17/3462; A61M 39/06; A61M 2039/0626; A61M 2039/0686;
(Continued)

(56) References Cited

U.S. PATENT DOCUMENTS 5,342,315 A   8/1994   Rowe et al.
5,524,633 A   6/1996   Heaven et al.
(Continued)

FOREIGN PATENT DOCUMENTS

CN   101474089 A   7/2009
CN   101478924 A   7/2009
(Continued)

OTHER PUBLICATIONS

Internation Search Report of PCT/CN2017/093602, dated Oct. 18, 2017.

*Primary Examiner* — Emily L Schmidt
(74) *Attorney, Agent, or Firm* — Erson IP (Nelson IP)

(57) ABSTRACT

The invention discloses a trocar seal membrane with concave-channel structure. Said seal membrane comprises a proximal opening, a distal aperture, and a sealing wall from the distal aperture extending to the proximal opening, said sealing wall comprising a proximal surface and a distal surface, said distal aperture formed by a scaling-lip for accommodating the inserted instrument and formed a gas-tight seal, said sealing-lip comprising a longitudinal axis and a transverse plane substantially perpendicular to said axis. In the lip-adjacent area, said sealing wall comprises the main rotary-wall and a plurality of concave-channel each of the concave-channels includes two side sealing-walls, which are defined by both edges and extending laterally outward from the sealing-lip and gradually widening. Said concave-channels have the functions of enlarging hoop circumference, reducing the wrapped area, improving lubrication reliability, increasing the axial tensile stiffness, etc., thereby, greatly reducing the frictional resistance and the stick-slip.

9 Claims, 13 Drawing Sheets

(52) U.S. Cl.
CPC .... *A61B 17/3498* (2013.01); *A61B 2017/00862* (2013.01); *A61B 2017/347* (2013.01); *A61M 2039/0633* (2013.01)

(58) Field of Classification Search
CPC .. A61M 2039/0633; A61M 2039/0653; A61M 2039/0673; A61M 2039/064; A61M 2039/0646; A61M 39/0606
See application file for complete search history.

(56) References Cited

U.S. PATENT DOCUMENTS

| | | |
|---|---|---|
| 5,545,142 A | 8/1996 | Stephens et al. |
| 5,827,228 A | 10/1998 | Rowe |
| 7,112,185 B2 | 9/2006 | Hart et al. |
| 7,591,802 B2 | 9/2009 | Johnson et al. |
| 2007/0255218 A1* | 11/2007 | Franer ............. A61B 17/3462 604/167.02 |
| 2011/0040255 A1 | 2/2011 | Schweitzer et al. |

FOREIGN PATENT DOCUMENTS

| | | |
|---|---|---|
| CN | 101480354 A | 7/2009 |
| CN | 103169528 A | 6/2013 |
| CN | 103505268 A | 1/2014 |
| CN | 204072247 U | 1/2015 |
| CN | 204428125 U | 7/2015 |
| CN | 106137340 A | 11/2016 |
| EP | 0994740 A1 | 4/2000 |

* cited by examiner

TROCAR SEAL MEMBRANE WITH CONCAVE-CHANNEL STRUCTURE

CROSS-REFERENCE TO RELATED APPLICATIONS

This application is a continuation of International Patent Application No. PCT/CN2017/093602 with a filing date of Jul. 20, 2017, designating the United States, now pending, and further claims priority to Chinese Patent Application No. 201610622263.5 with a filing date of Aug. 2, 2016. The content of the aforementioned applications, including any intervening amendments thereto, are incorporated herein by reference.

TECHNICAL FIELD

The present invention relates to a minimally invasive surgical instrument, and in particular, to a trocar sealing element.

BACKGROUND OF THE PRESENT INVENTION

A trocar is a surgical instrument, that is used to establish an artificial access in minimally invasive surgery (especially in rigid endoscopy). Trocars comprise in general a cannula and an obturator. The surgical use of trocars generally known as: first make the initial skin incision at the trocar insertion site, then insert the obturator into the cannula, and then together they facilitated penetration of the abdominal wall through, incision into the body cavity. Once penetrated into the body cavity, the obturator is removed, and the cannula will be left as access for the instrument get in/out of the body cavity.

In rigid endoscopy surgery it is usually necessary to establish and maintain a stable pneumoperitoneum for the sufficient surgical operation space. The cannula comprises a sleeve, an outer body, a seal membrane (also known as instrument seal) and a duck bill (also known as closure valve). Said cannula providing a channel for the instrumentation in/out of the body cavity, said outer body connecting the sleeve, the duck bill and the seal membrane into a sealing system; said duck bill normally not providing sealing for the inserted instrument, but automatically closing and forming a seal when the instrument is removed; said seal membrane accomplishing a gas-tight seal against the instrument when it is inserted.

In a typical endoscopic procedure, it is usually set up 4 trocars (access), i.e. 2 sets of small diameter cannula (normally 5 mm in diameter), and 2 sets of large diameter cannula (normally 10~15 mm in diameter). Instruments, in general passing through a small cannula are only for ancillary works; herein one large cannula as an endoscope channel, and the other large cannula as the main channel for surgeon to perform surgical procedures. Through said main channel thereof, 5 mm diameter instruments used in approximately 80% of the procedure, and said large cannula used in approximately 20% of the procedure; furthermore, 5 mm instruments and large diameter instruments need to be switched frequently. The small instruments are mostly used, so that the sealing reliability of which is more important. The large instruments are more preferably used in a critical stage of surgery (Such as vascular closure and tissue suturing), therein switching convenience and operational comfort are more important.

FIG. 1 and FIG. 2 depict a typical 12 mm diameter cannula 700. Said cannula 700 comprises a lower housing 710, an upper housing 720, a seal membrane 730 which sandwiched between the lower housing 710 and the upper housing 720, and a duckbill seal 750. Said lower housing 710 including center hole 713 defined by an, elongated tube 711. Said upper housing 720 including the proximal hole 723 defined by the inner wall 721. Said membrane 730 including a proximal opening 732, a distal aperture 733, a sealing-lip 734, a frustum sealing wall 735, a flange 736 and an outer floating portion 737. Said distal opening 733 formed by a sealing-lip 734. Said sealing-lip 734 defining a longitudinal axis 741, transverse plane 742 substantially perpendicular to said axis 741; define the angle between the rotary-generating line (or generatrix) of the frustum sealing wall 735 and the transverse plane 742 as a guide angle ANG1.

As illustrated in FIG. 1, when a 5 mm diameter instrument inserted, it is approximately considered that only hoop force generated by the deformation, of the sealing-lip 734, ensures a reliable seal for the instrument. It is nevertheless favorable to operate the instrument from various extreme angles in surgery. (here's a lot space left for the 5 mm-instrument to move radially in the 12 mm diameter cannula, so that greater, radial force would be taken by the sealing-lip 734. Therefore, the sealing-lip 734 should have sufficient hoop force for the inserted 5 mm diameter instrument to ensure its sealing reliability thereof.

As illustrated, in FIG. 2, drawing a cylinder of Di (Di>5 mm) to cut the sealing wall 735 forms an intersecting line 738. It is easy to understand for those skilled in the art, when an Di diameter instrument, is inserted, the strain (stress) of said sealing wall 735 in the area from the sealing-lip 734 to the intersecting line 738 will be larger, so the area refer to as lip-adjacent area (or concentration stress area). While the strain (stress) of said sealing wall 735 from the intersecting line 738 to the flange 736 is small. However, the different diameter (Di value) makes the boundary range of the lip-adjacent area (or concentration stress area) change larger or smaller. For the convenience of quantification, it is defined when designed as the maximum diameter of the surgical instrument passing through the seal membrane, the area from the sealing-lip 734 to the intersection line 738 is the lip-adjacent area.

As illustrated in FIG. 3, when a large diameter instrument is inserted (e.g. 12.8 mm), the sealing-lip 734 will expand to a suitable size to accommodate the inserted instrument; said, sealing wall 735 is divided into two portions: a conical wall 735c and a cylindrical wall 735d; said cylindrical wall 735d wrapped around the outer surface of the instrument to form a wrapped area with a high concentration of stress. Defining the intersecting line of the conical wall 735c and the cylindrical wall 735d as intersecting line 738a. When the instrument is removed, said sealing wall 735 return to natural state, and said intersecting line 738a spring-back to a ring radius of Dx, defined as intersecting line 735b, (not shown in FIG); said intersecting line 738b is a bending boundary line when inserting a large diameter instrument. The angle between the rotary generating line of said conical wall 735c and the transverse plane 742 defines as ANG2, ANG2>ANG1; that is, when the large-diameter instrument is inserted, said sealing wall 735 rotates and stretch around its intersection line of said flange 736. Defining the height of the cylindrical wall 735d as Ha, not a fixed value; the factors such as different size of said distal aperture, different size of said sealing-lip, different thickness of said sealing wall, different said guide angle or different diameter of inserted instrument, make Ha different.

The instrument inserted into the sealing membrane and moved during surgical procedure, there is large frictional resistance between the wrapped area and the inserted instrument. Said large frictional resistance is normally easy to cause the seal inversion, poor comfort of performance, fatigue performance, even result in cannula insecurely fixed on the patients abdominal wall etc., such that the performance of cannula assembly is affected.

Among the defects caused by the large frictional resistance, the seal inversion, is one of the most serious problems that affecting the performance of the cannula. As illustrated in FIG. 4, when a large diameter instrument is removed, easily cause seal inversion. When inversion happened, said sealing wall 735 divided into a cylindrical wall 735e, a conical wall 735f, and a conical wall 735g; said cylindrical wall 735e wrapped around the outer surface of the instrument to form a wrapped area with a high concentration of stress. Defining the height of the cylindrical wall 735e to be Hb, normally Hb>Ha; that is, the frictional resistance when the instrument is removed greater than it when the instrument is inserted, this difference affects the surgeon's operating feeling and even make the surgeon confused. More seriously, the inversion of the seal membrane may stretch into the proximal hole 723, that is the seal membrane positioned between the instrument and the inner wall 721 gets completely jammed. Measures for preventing the seal inversion are respectively disclosed in U.S. Pat. Nos. 7,112,185 and 7,591,802, and those measures can effectively reduce the probability of inversion but not completely solve the problem.

The simplest way to reduce the frictional resistance is reducing the coefficient of friction between the two contacting surfaces with grease, but the reliability of this way is not good. During procedures, due to instruments long-term repeated scraping with the seal membrane and repeated switching, it is easy to erase the grease off and carried away, resulting in bad lubrication.

A protector assembly adjoined by a seal membrane is disclosed in U.S. Pat. No. 5,342,315. Said protector to permit the sharp edge of the instrument to pass through the opening in the seal membrane without causing damage to the seal membrane, and the surface friction coefficient of the protector assembly is smaller than the surface friction coefficient of the seal membrane, which results in less frictional drag, but the lip-adjacent area is normally not completely covered by the protector assembly.

A seal member with ribs (or projections) is disclosed in U.S. Pat. No. 5,827,228, that is a plurality of spaced ribs provided to extend outwardly from center hole to reduce surface contact between the inserted instrument and the seal member, and thereby reducing the frictional resistance, a similar ribs which disclosed in EP 0994740 also reducing surface contact and strengthen the tensile of the seal member oriented to axial.

A sealing element comprising a flexible wall closed annularly with the edges foldable in a wave-like manner is disclosed in U.S. Pat. No. 7,842,014, wherein the wall bears a wave-like sealing-lip and is a wavy pleated seal body, in such manner it can enlarge hoop circumference, and reduce the hoop force to a certain extent.

Chinese invention application CN 101480354 A (currently rejected) discloses a seal member containing an easily deformable groove, wherein is characterized in that it has a plurality of easily deformable, grooves on the conical surface of the seal member from the sealing-lip; said the thickness of the deformable groove wall is much smaller than the thickness of the conical surface wall, primary take advantage of the elongation of the deformable groove to accommodate the inserted large diameter instrument.

Although, in the prior art many solutions for reducing the frictional resistance have been disclosed, these solutions basically only propose measures from one certain factor affecting frictional resistance, the effect of which is small or not obvious. Some modifications solved a certain defects may lead to cause another bug. Such as, reinforcing ribs on the seal membrane to reduce surface contact, meanwhile strengthen the tensile of the seal membrane; or a deformable groove with a thickness much smaller than that of a truncated conical surface can cause the deformable groove to be easily damaged; due to the adoption of said wave-like sealing-lip which enlarge hoop circumference, the sealing reliability will be sacrificed when a 5 mm diameter instrument is inserted, if the wave-like sealing-lip is used but without enlarge hoop circumference, the wave-like sealing-lip will lose its improvement effect. In summary there are many factors affecting the frictional resistance, and the comprehensive effects of various factors must be considered in the perspective of mechanics and tribology.

The seal membrane is preferably produced from rubber such as natural rubber, silicone or polyisoprene, its mechanical properties including super elastic and viscoelastic Although the mechanical model of the rubber deformation process is complicated, it can still apply the generalized Hooke's law to describe approximatively its elastic behavior; and Newton's internal friction law to describe the viscous behavior. Research suggests that the main factors affecting the friction of the two surfaces in contact between the rubber and the instrument include: the smaller the friction coefficient of said two surfaces, the smaller the friction is; the better lubrication condition of said two surfaces in contact, the friction smaller is; the smaller normal pressure of said two surfaces, the friction smaller is. Comprehensively considering the above factors the present invention proposes better solutions for reducing the frictional resistance between the seal membrane and the inserted instrument.

In addition to said frictional resistance greatly affecting the performance of the cannula assembly, the stick-slip of the seal membrane is another main factor affecting the performance of trocar. Said stick-slip means that when the instrument moves longitudinally in the sleeve, the sealing-lip and lip-adjacent area sometimes are relatively statically attached to the instrument (at this point, the friction between the instrument and the seal membrane is mainly static friction.); but sometimes it produced a relatively slippery phenomenon with the instrument (at this point, the friction between the instrument and the seal membrane is mainly dynamic friction.); and said static friction is much greater than said dynamic friction. The two frictions alternately occur, which causes the movement resistance and speed of the instrument in the seal membrane to be unstable. It is easy to be understood for those skilled in the art, that in minimally invasive, surgery the surgeon can only use surgical instruments to touch (feel) the patient's organs and observe a part of the working head of the instruments through endoscopic image system. In this case where the vision is limited and it cannot be touched, the surgeon typically uses the feedback of the resistance when moving instruments as one of the information to judge whether the operation is abnormal nor not. The stick-slip affects the comfort of operation, the accuracy of positioning, and even induces the surgeon to make false judgment.

During the surgical application of the cannula, the stick-slip is difficult to avoid, but can be reduced. Researches have shown that said stick-slip is, affected by two main factors: one is that the smaller the difference between the maximum static friction and the dynamic friction, the weaker the stick-slip is; the other is that the larger the axial tensile stiffness of the seal membrane, the weaker the stick-slip is. Avoiding excessive the hoop force between the seal membrane and the instrument, reducing the two surfaces contacted, maintaining good lubrication, respectively, can reduce the difference between the maximum static friction and the dynamic friction, thereby reducing stick-slip, meanwhile, increasing the axial tensile stiffness of the seal membrane also helps to reduce the stick-slip phenomenon. The invention also proposes measures for improving stick-slip.

In summary, so far, there is, no cannula that can effectively solve the said problems.

SUMMARY OF PRESENT INVENTION

In conclusion, one object of the invention is to provide a trocar seal membrane, said seal membrane comprises a proximal opening, a distal aperture, and a scaling wall from the distal aperture extending to the proximal opening, said distal aperture formed by a sealing-lip for accommodating the inserted instrument and forming a gas-tight seal. Said the sealing wall includes a proximal surface and a distal surface. Said seal membrane can ensure a reliable seal for the inserted 5 mm instrument, and reduce frictional resistance and improve stick-slip when a large-diameter instrument is inserted.

As described in the background, the wrapped area formed by the sealing-lip and the lip-adjacent area, when, a large diameter instrument inserted, is the major factor cause of frictional, resistance. For reducing said frictional resistance, comprehensive consideration should be given such as reducing the radial stress between the instrument and the seal membrane, reducing said wrapped area, and reducing the actual contact area of the two surfaces. It is easy to understand for those skilled in the art that in accordance with the generalized Hooke's law and Poisson effect, enlarge hoop circumference, and reduce hoop strain (stress), thereby reducing radial strain (stress). But it should be noted that it is impossible to enlarging the hoop circumference in order to reduce the strain of the sealing-lip which will sacrifice sealing reliability when applying 5 mm instruments. Since the stress in the lip-adjacent area is highly concentrated when applying a large diameter instrument, the hoop circumference of the lip-adjacent area should be, rapidly increased. In regard to outside the lip-adjacent area, since the strain (stress) is small, it is not necessary to adopt measures to enlarge the hoop circumference. In addition, enlarging the hoop circumference, in the meantime increasing the axial tensile stiffness in the lip-adjacent area and maintain good lubrication (reducing difference between the maximum static friction and dynamic friction thereby the stick-slip in the lip-adjacent area is improved.

In one aspect of the invention, said seal membrane comprises a proximal opening, a distal aperture, and a sealing wall from the distal aperture extending to the proximal opening, said sealing wall comprising a proximal surface and a distal surface. Said distal aperture formed by a sealing-lip for accommodating the inserted instrument forms a gas-tight seal. Said sealing-lip comprises a longitudinal axis and a transverse plane substantially perpendicular to said axis. Said sealing wall in the lip-adjacent area, comprises the main rotary-wall and a plurality of concave-channels, which is recessed from the proximal surface of the main rotary-wall toward the distal surface and divide the main rotary-wall into multiple areas. In the lip-adjacent area, each of said concave-channels includes two side sealing-walls, which are defined by both edges and extending laterally outward, from the sealing-lip and gradually widening. Said concave-channels has the functions of enlarging hoop circumference, increasing the axial tensile stiffness, reducing the wrapped area, reducing, the actual contact area of the two surfaces between the instrument and the seal membrane. In one embodiment, the sealing-lip is circular, and the section of said concave-channels is approximately U-shaped. Optionally, the internal width of said concave-channels in the lip-adjacent area is B, wherein 0.5 mm≤B≤mm. Said seal membrane also includes a flange at which the main rotary-wall extend to be intersected, or simultaneously the main rotary-wall and said concave-channels extend to be intersected, and, an outer floating portion including at least one lateral pleat extending from the flange to the proximal opening.

Optionally, in one embodiment, this geometric relationship, herein is the angle between the two edges of the side sealing-wall of concave-channel in the lip-adjacent area, conforms to the following equation:

$$\theta \geq \arctan \frac{9\pi R(R_i - R)\cos\alpha}{P(R_i + 9R)(R - R_0)}$$

Where:
θ=the angel between two edges of the concave-channel side sealing-wall in the lip-adjacent area;
α=the angle between the generating line of the main rotary-wall and the transverse plane surface in the lip-adjacent area (guide angle);
arctan=arctangent function;
cos=cosine function;
π=circumference ratio;
R=radius;
$R_i$=the largest radius designed for the surgical instrument passed through the seal membrane;
$R_0$=radius of the sealing-lip;
P=number of concave-channel.

While Outside the lip-adjacent area, the width of the side sealing-wall does not conform to the above equation, the side sealing-wall is gradually smaller. This, such as it is, can, simplify mold processing and increase production efficiency of the seal membrane, and reducing the space occupied by the lateral movement of the sealing assembly, so that the size of trocar can be designed to be smaller.

In one aspect of the invention, said seal membrane comprises a proximal opening, a distal aperture, and a sealing wall from the distal aperture extending to the proximal opening, said sealing wall, comprising a proximal surface and a distal surface, said distal aperture formed by a sealing-lip for accommodating the inserted instrument forms a gas-tight seal; In the lip-adjacent area, said sealing wall comprises the main rotary-wall and a plurality of concave-channels, each of the concave-channels includes two side sealing-walls, which are areas defined by both sides and extending laterally outward from the sealing-lip and gradually widening along longitudinal axis of the sealing-lip; outside the lip-adjacent area, the width of the side sealing-wall is rapidly reduced first, and then extending laterally outward in the case of maintaining a constant width.

In the present embodiment the depth of said concave-channels increase along longitudinal axis of the sealing-lip and then rapidly decreases to a certain depth, and then extending laterally outward in the case of maintaining a constant depth, that is, the concave-channels are ladder-shaped. Said ladder-shaped concave-channels can enhance the axial tensile stiffness, reduce the wrapped area, and reduce the actual contact area of the two surfaces between the instrument and the seal membrane after inversion to a large extent.

In another aspect of the invention, said seal membrane comprises a proximal opening, a distal aperture, and a sealing wall from the distal aperture extending to the proximal opening. Said distal aperture formed by a sealing-lip for accommodating the inserted instrument forms a gas-tight seal. Said sealing wall comprises 8 V-shaped pleats and 8 U-shaped concave-channels arranged alternately. Said 8 V-shaped pleats contribute to enhance the axial tensile stiffness, reduce the wrapped area, and reduce the actual contact, area of the two surfaces between the instrument and the seal membrane; while said U-shaped concave-channels can enlarge the hoop circumference in the lip-adjacent area.

In another aspect of the invention, said seal membrane comprises a proximal opening, a distal aperture, and a sealing wall from the distal aperture extending to the proximal opening. Said distal aperture formed by a sealing-lip for accommodating the inserted instrument forms a gas-tight seal. In the lip-adjacent area, said sealing wall comprises the main rotary-wall and a plurality of concave-channels, which is recessed from the proximal surface of the main rotary-wall toward the distal surface and divide the main body wall into multiple areas. Each of the concave-channels includes two side sealing-walls, which are areas defined by both edges and extending laterally outward from the sealing-lip and gradually widening along longitudinal axis of the sealing-lip. In the present embodiment, wherein one portion of concave-channel section is U-shaped and the other portion is V-shaped. In the present embodiment said the sealing-lip is cylindrical.

Another object of the invention is to provide a trocar seal assembly, which including a lower retainer ring, a seal membrane, a protection device, an, upper retainer ring, an upper body and an upper cover. Said the seal membrane and said protection device are sandwiched between the lower retainer ring and the upper retainer ring, said protection device permit the sharp edge of the instrument to pass through without causing perforations or tears to the seal membrane; said seal membrane also includes a flange at which the main rotary-wall extends to be intersected, and an outer floating portion including at least one lateral pleat extending from the flange to the proximal opening. Said outer floating portion makes said seal membrane and protector float laterally in the housing formed by the upper body and the cover.

It is believed that the above invention or other objects, features and advantages, will be understood with the drawings and detailed description.

DESCRIPTION OF THE DRAWINGS

Amore complete appreciation of this invention, and many of the attendant advantages thereof will be readily apparent as the same becomes better understood by reference to the following detailed description, where.

In all views, the same referred number shows the same element or assembly.

DETAILED DESCRIPTION OF PREFERRED EMBODIMENTS

Embodiments of the invention are disclosed herein, however, it should be understood that the disclosed embodiments are merely examples of the invention, which may be implemented in different ways. Therefore, the invention is not intended to be limited to the detail shown, rather, it is only considered as the basis of the claims and the basis, for teaching, those skilled in the art how to use the invention.

Figure 1:
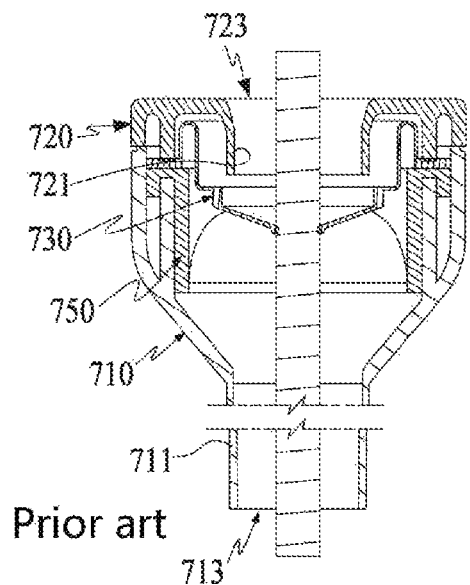
FIG. 1: shows a simulated distorted view of the cannula with the 5 mm diameter instrument inserted in the prior art.
Figure 2:
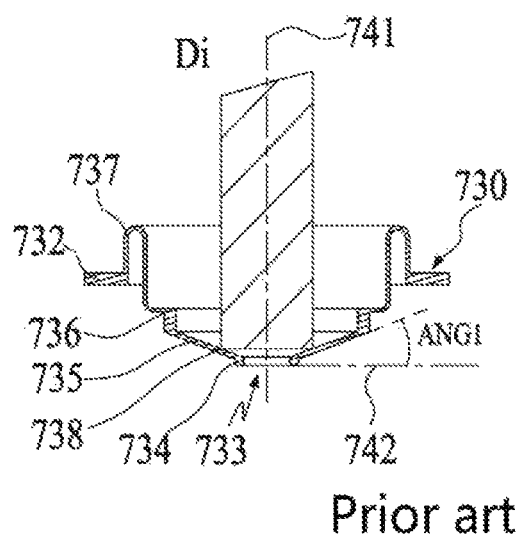
FIG. 2: shows a detailed view of the seal membrane 730 in the prior art.
Figure 3:
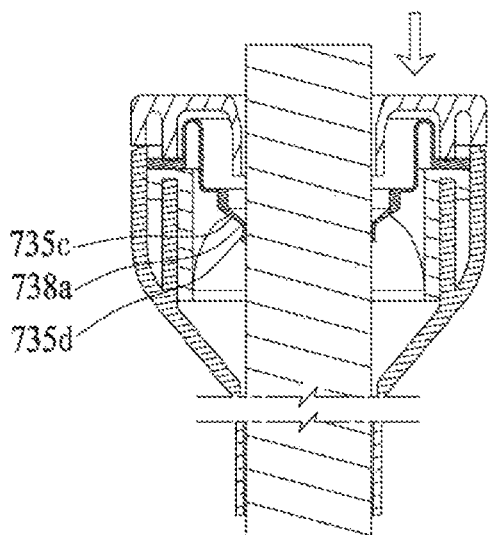
FIG. 3: shows a simulated distorted view of the cannula with the 12.8 mm diameter instrument inserted in the prior art.
Figure 4:
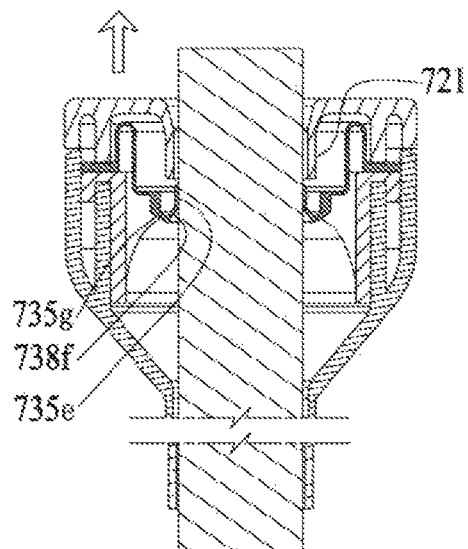
FIG. 4: shows a simulated distorted view of the cannula with the 12.8 mm diameter instrument removed in the prior art.
Figure 5:
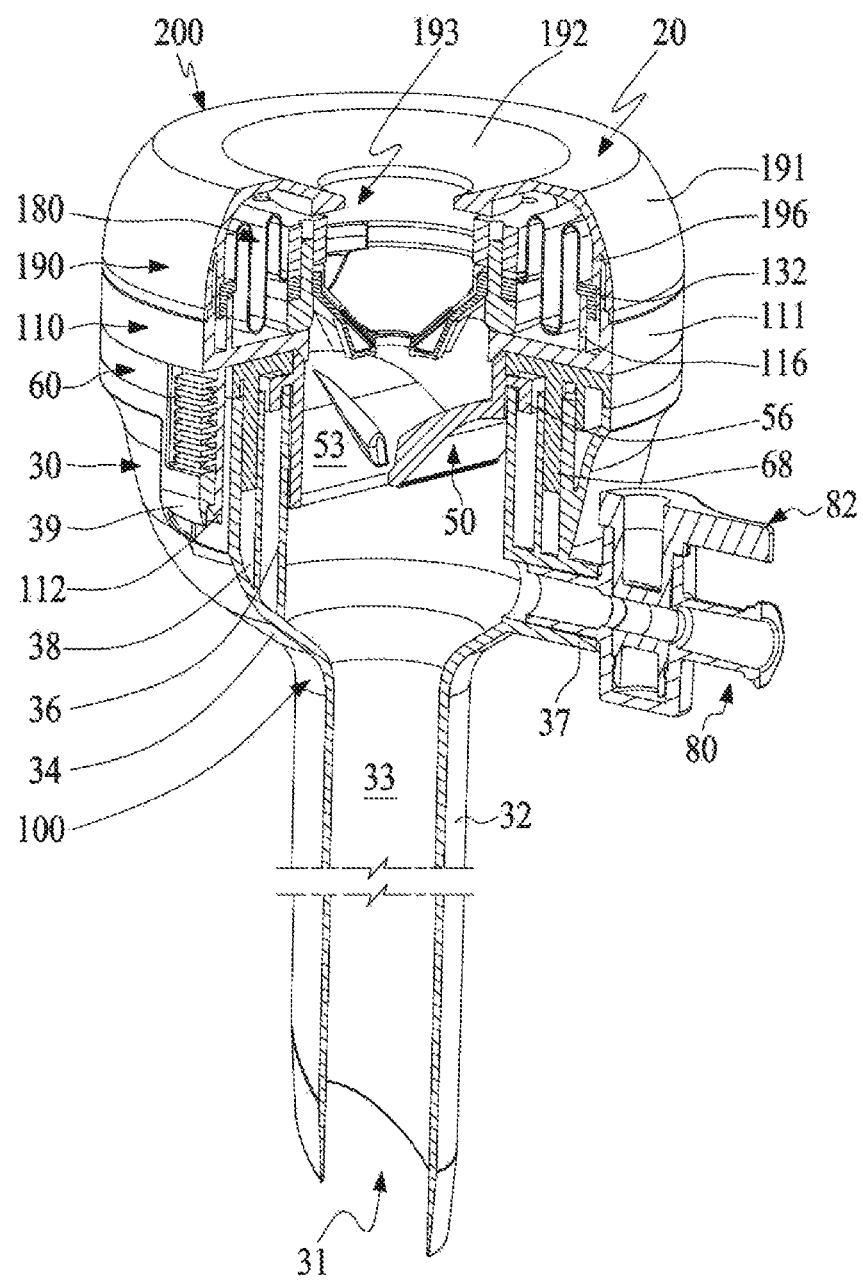
FIG. 5: shows a 3D perspective partial sectional view of the cannula in the invention.

FIG. 5 shows an overall view of the structure of trocar. A typical trocar comprises an obturator 10 (not shown) and a cannula 20. The cannula 20 comprises an open proximal end 192 and an open distal end 31. In a typical embodiment, said obturator 10 passes through said cannula 20, together they facilitated penetration, of the abdominal wall through incision into the body cavity. Once penetrated into the body cavity, the obturator 10 is removed, and the cannula 20 will be left as access for the instrument get in/out of the body cavity. Said proximal end 192 in the external position of the patient and said distal end 31 in, the internal position. A preferred cannula 20 can be divided into the first seal assembly 100 and the second, seal assembly 200. Locking receptacle 39 in said seal assembly 100 can be locked with snap-in projection 112 in said seal assembly 200. The cooperation of snap-in projection 112 and the locking receptacle 39 can be quick, release by one hand. The main purpose is for convenience of taking out tissues or foreign matter from the patient in the surgery. There are multiple ways to implement the quick release connection of said seal assembly 100 and assembly 200. In addition to the structure shown in this embodiment, a threaded connection, a rotary snap-in or other quick lock structure also may be applied. Alternatively, said assembly 100 and assembly 200 can be designed as a structure that can not be split quickly.

FIG. 5 shows the composition and assembly relationship of the first seal assembly 100. The lower body 30 includes an elongated tube 32, which defines the sleeve 33 passed through the distal end 31 and is connected to the outer housing 34. Said lower body 30 comprises an inner wall 36 supporting duck bill seal and a valve bore 37 that communicates with the inner wall 36. The plunger 82 mounted in the valve body 80, the said two are mounted into said valve bore 37. The flange 56 of the duck bill seal 50 is sandwiched between the inner wall 36 and the lower cover 60. There are various ways of fixing between the lower cover 60 and the lower body 30, such as the interference fit, ultrasonic welding glue bonding, and snap fastening. 4 cylinders 68 of said lower cover 60, in this embodiment, 4 holes 38 of said lower body 30 are adopted to interference fit, so that the duckbill seal 50 is in the compressed state. Said tube 32, said the inner wall 36, said duck bill seal 50, said valve body 80 and said plunger 82 together are comprised the first chamber. Said duck bill seal 50, in this embodiment, is a single-slit, while other types of closure valves may also be used, including flapper valves, multi-silted duck bill valves. When the instrument is passed through said duck bill seal 50, the duckbill 53 will be opened, but it generally does not provide a complete seal against the instrument. When the instrument is removed, said duckbill 53 closed and substantially prevents insufflation fluid from escaping through the first chamber.

FIG. 5 shows the composition and assembly relationship of the second seal assembly 200. The seal membrane assembly 180 is sandwiched between the upper cover 110 and the upper body 190. The proximal end 132 of the seal membrane assembly 180 is secured between the inner ring 116 of the upper cover 110 and the inner ring 196 of the upper body 190. There are various secured ways between the upper cover 190 and the upper body 110, such as the interference fit, ultrasonic welding, glue bonding, and snap fastening. The connection method, shown in this embodiment, is the outer shell 191 of the upper body 190 and the outer shell 111 of the upper cover 110 are secured by ultrasonic welding, so that the proximal end 132 of the seal membrane assembly 180 is in the compressed state. The center hole 113 of said upper cover 110, said inner ring 116, and said seal membrane assembly 180 together are comprised the second chamber.

Figure 6:
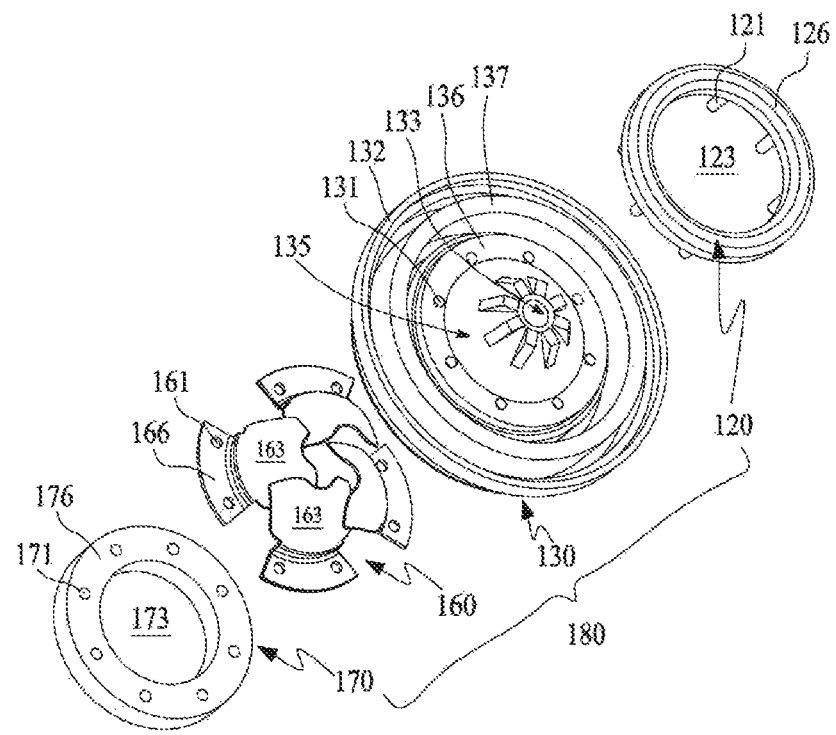
FIG. 6: shows an exploded view of the seal membrane assembly of the cannula in FIG. 5.
Figure 7:
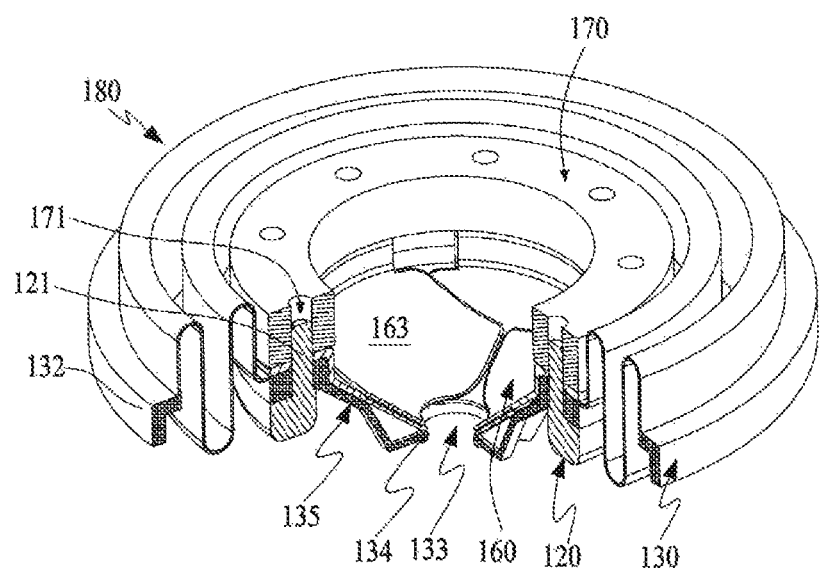
FIG. 7: shows a 3D perspective partial sectional view of the seal, membrane assembly in FIG. 6.
Figure 8:
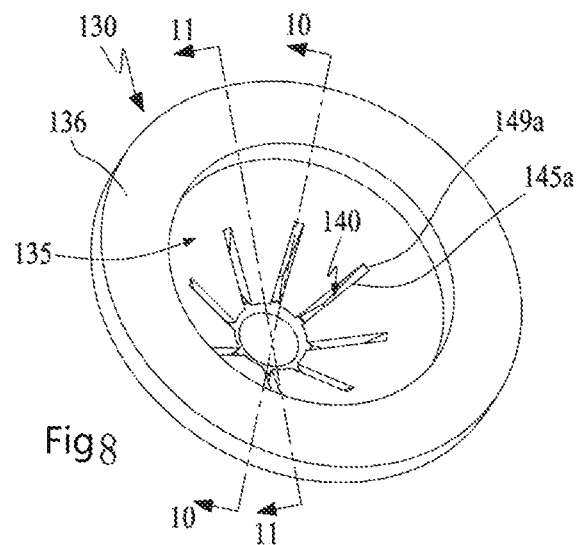
FIG. 8: shows a 3D perspective view of the seal membrane without the proximal end, and floating portion in FIG. 6.
Figure 9:
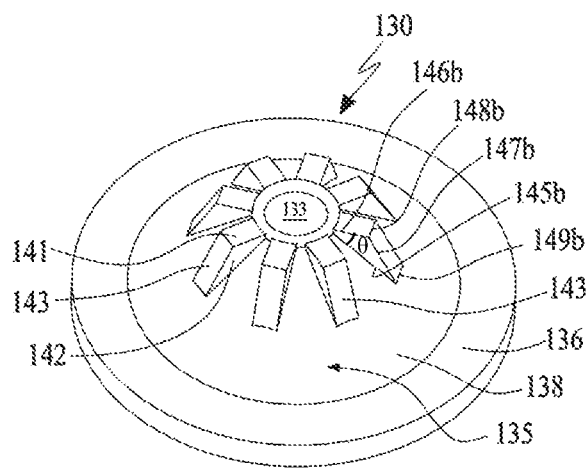
FIG. 9: shows a 3D perspective reserve view of the seal membrane in FIG. 8.
Figure 10:
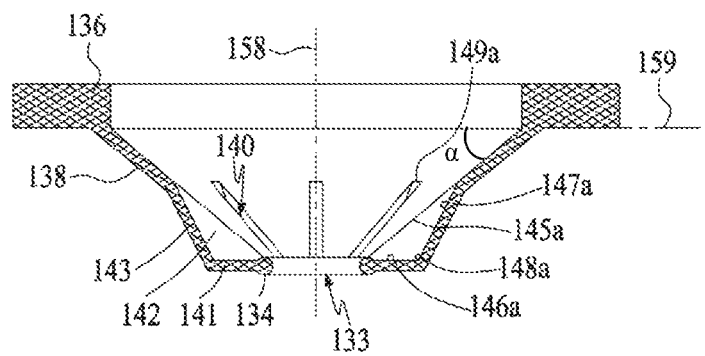
FIG. 10: shows a sectional view along line 10-10 in FIG. 8.
Figure 11:
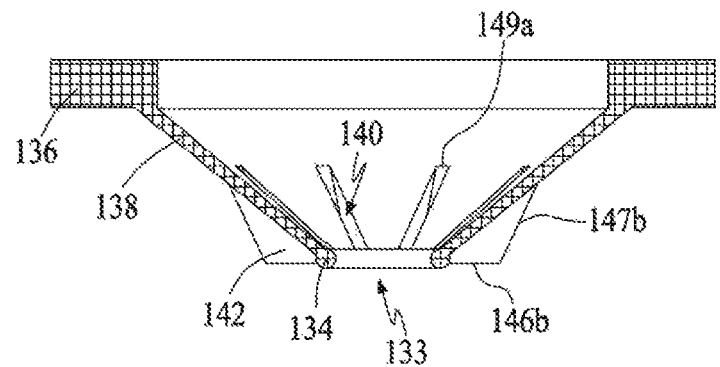
FIG. 11: shows a sectional view along line 11-11 in FIG. 8.

FIG. 6-7 illustrate the composition and assembly relationship of said seal membrane assembly 180, which including a lower retainer ring 120, a seal membrane 130, a protection device 160 and an upper retainer ring 170. Said the seal membrane 130 and said protection device 170 are sandwiched between the lower retainer ring 120 and the upper retainer ring 125, moreover, the cylinder 121 of the said lower retainer ring 120 is aligned with corresponding holes on other components in said seal membrane assembly 180. Said cylinder 121 and the bore 171 of the upper retainer ring 170 are adopted to interference fit, so that the whole seal membrane assembly 180 is in the compressed state. Said protection device 160 includes 4 protectors 163 arranged so as to protect a center sealing body of said seal membrane 130, herein permit the sharp edge of the instrument to pass through without causing perforations or tears to the seal membrane 130.

Said seal membrane comprises a proximal opening 132, a distal aperture 133, and a sealing wall extending from the distal end to the proximal end, said sealing wall comprising a proximal surface and a distal surface. Said aperture 133 formed by a sealing-lip 134 for accommodating an inserted instrument and forming a gas-tight seal. Said scaling-lip 134, in the present embodiment, is approximately circular, but said sealing-lip 134 may be not circular, defining its radius as Rlip, so the circumference of the sealing-lip is approximately equal to 2*Rlip*π(π=3.14159), usually the circumference of the sealing-lip is 11.8~13.8 mm. The section of said sealing-lip is circular, usually its radius is 0.35 to 0.5 mm diameter.

Said the seal membrane 130 also includes the flange 136; the sealing wall 135 has one end connected to the sealing-lip 134 and the other end connected to the flange 136; the floating portion 137 has one end connected to the flange 136 and the other end connected to said proximal end 132. Said flange 136 for mounting the protector device 160. Said floating portion 137 including one or several plurality of radial (lateral) pleats, so that the entire seal membrane assembly 180 can float in the assembly 200.

Said assembly 180 can be made from a variety of materials with a range of different properties. For instance, said seal membrane 130 is made of a super elastic material such as silicone or polyisoprene; said protector device 160 is made of a semi-rigid thermoplastic elastomer; and said second retainer ring 120 and said first retainer ring 170 are made of a relatively hard rigid material such as polycarbonate.

FIG. 8-11 show more detailed depiction of the seal membrane 130 in the first embodiment of the invention. In order to reduce the production cost, the seal membrane 130 is preferably designed as a monolithic part, but can also be designed as an inner seal body and an outer floating portion, separated from the flange 136. The first embodiment is mainly directed to the improvement of the inner seal body. To simplify the description, the outer floating portion and the proximal end are not shown in the subsequent description of the seal membrane. Defining a transverse plane 159 that is generally perpendicular to the longitudinal axis 158.

Said sealing wall 135, which can be approximately frustum, approximately hemispherical, or an irregularly rotating surface. In this embodiment, said wall 135 is formed in an approximately conical arrangement surrounding the sealing-lip 134. Said wall 135 including the main rotary-wall 138 and a plurality of Concave-channels 140. Said Concave-channels 140 are recessed from the proximal surface of the main-rotary-wall 138 towards the distal surface, and the opening of Concave-channel is towards, the proximal surface. Said Concave-channels 140 extend laterally outward from the sealing-lip 134, and the depth of Concave-channels 140 gradually increases in the lip-adjacent, area, and the depth of which rapidly decreases outside the lip-adjacent area. The measurement method of the Concave-channels depth is: the shortest distance from the point at the bottom of the Concave-channels to the main rotary-wall along longitudinal axis. In the lip-adjacent area, said a plurality of Concave-channels 140 are divided the main rotary-wall 138 approximately into a plurality of portions.

Said Concave-channel 140 includes a lower sealing-wall 141, a side sealing-wall 142 and a tilted sealing-wall 143. The first edge of said side sealing-wall 142 and said the main rotary-wall 138 formed an intersection line 145a, 145b; the second edge of said side sealing-wall 142 and said lower sealing-wall 141 formed an intersection line 146a, 146b; the third edge of said side sealing-wall 142 and said tilted sealing-wall 143 formed an intersection line 147a, 147b; said tilted sealing-wall 143 and said lower sealing-wall 141 formed an intersection line 148a, 148b; and said tilted sealing-wall 143 and said main rotary-wall 138 formed an, intersection line 149a, 149b. Defining the angle between said intersection line 145a (145b) and said transverse plane surface 159 as $\alpha$, and $0 \leq \alpha < 90°$ (when $\alpha$ is 0°, the rotary wall is parallel to the transverse plane actually this can happen; When $\alpha$ is close to 90°, the main rotary-wall and the transverse, plane are approximately vertical, in this case, the wrapped area is larger when a large diameter instrument is inserted, normally the angle $\alpha$ should be <50°).

Figure 12:
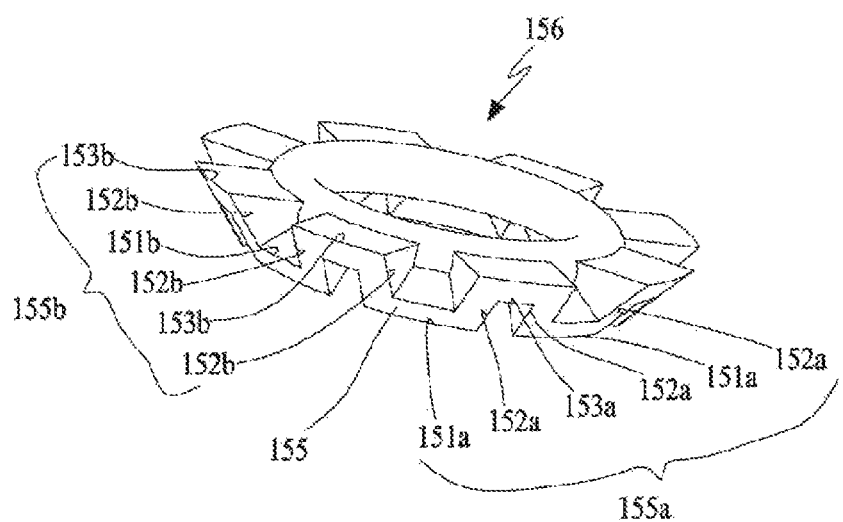
FIG. 12-13: shows a segmentation view of the seal membrane after the circumferential cutting separation, in FIG. 9.
Figure 13:
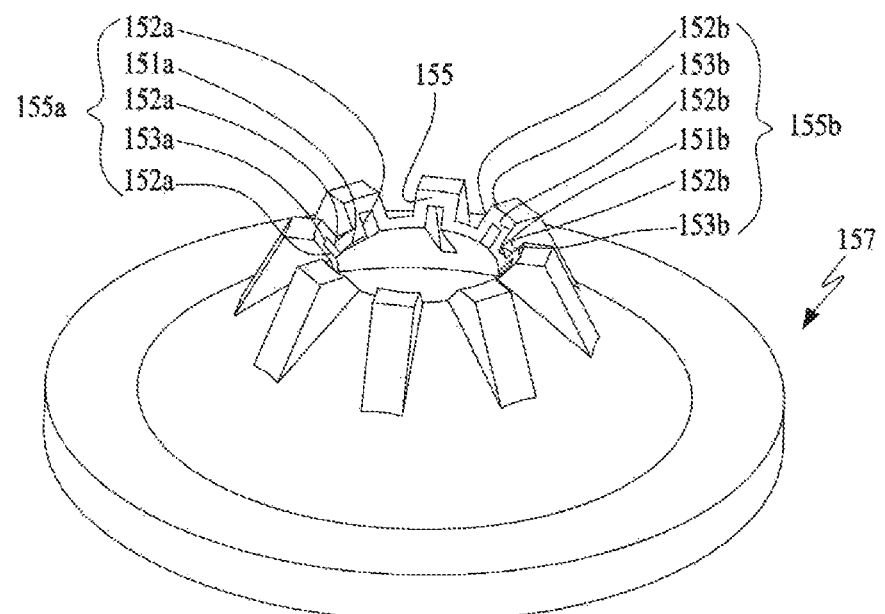

As FIG. 12-13 has shown, in an alternative embodiment, that the thickness of said scaling wall 135 is substantially uniform, that is, the thickness of the main rotary-wall 138, the lower sealing-wall 141, and the side sealing-wall 142 are substantially equal, so that the deformation of the sealing wall 135 is substantially uniform. However, the thickness of said substantially uniform wall should not be limited to the values of the absolute equality. When, the number of said Concave-channels is numerous, the thickness of the side sealing-wall 143 can be 0.05~0.25 mm thinner than the thickness of the lower sealing-wall 141 (or the side sealing-wall 142) for convenience of manufacture (for example, to, enhance the strength of the mold at the Concave-channel), or considering the tolerance. The thickness value of the lower scaling-wall 141, the side sealing-wall 142, and the tilted scaling-wall 143 is small, for convenience of quantification, the thickness ratio between the lower sealing-wall 141 (or the side sealing-wall 142) and said tilted scaling-wall 143 within 1~1.5, which still approximately consider that the thickness of the sealing wall 135 is substantially uniform and still does not deviate from the scope of the invention.

The sealing wall 135, in the present embodiment, comprises 8 linear Concave-channels, however, a greater number or smaller of non-linear Concave-channel may be adopted. The side sealing-wall 142 of the present embodiment is substantially parallel to the longitudinal axis 158, and in the lip-adjacent area, make a arbitrarily section plane that parallel to said axis 158 and meanwhile perpendicular to side sealing-walls 142, the intersected profile formed by said section plane and said Concave-channels 140 is approximately U-shaped (the intersected profiles of other Concave-channels are also defined in this way). However, for convenience of manufacture, such as mold unloading, said side sealing-walls 142 may not be parallel to the longitudinal axis 158; that is, the section of the Concave-channel 140 is approximately trapezoidal, even approximately V-shaped.

Taking the longitudinal axis 158 as a rotary axis, make a cylindrical surface with a radius R1 and intersects with said main rotary-wall 138 to form an intersection line, and create cutting plane M1 through said intersection line and perpendicular to the generating line of the main rotary-wall 138 (with the axis 158 as rotary axis). Said cutting plane M1 divides the seal membrane 130 into an inner portion 156 (as in FIG. 11) and an outer portion 157 (FIG. 12). Said cutting plane M1 intersects the main rotary-wall 138 to form a plurality of intersection lines 151a and 151b. Said cutting plane M1 intersects the side sealing-wall 142 to form a plurality of intersection lines 152a and 152b, and said cutting plane M1 intersects said inner side sealing-wall 141 to form a plurality of intersection lines 153a and 153b. The plurality of segments 151a, 152a, 153a are formed an annular intersection line 155a; the plurality of segments 151b, 152b, 153b are formed an annular intersection line 155b, and the section 155 defined by said annular intersection line 155a and 155b.

As shown in FIG. 12-13, it is obvious that the circumference L1 of the intersection line 155a (155b) is much larger than $2*\pi*R1$, that means the Concave-channel plays a role in enlarging hoop circumference, and the difference between L1 and $2*\pi*R1$ is approximately equal to $2*P$ times the length L2 of the intersection line 152a (152b) (P is the number of Concave-channels). That is, the side sealing-wall 143 actually plays a role in enlarging hoop circumference. With the prerequisite of the Concave-channels width meeting the needs of the manufacturer, enlarging the width of the Concave-channel does not mean have a larger hoop circumference.

Those skilled in the art can understand that there must be some R1 value making the outer portion 157, which is divided by the cutting plane M1, to start from the section 155, the main change of its shape is shown as local bending deformation and macroscopic displacement of the seal membrane, rather than the overall microscopic molecular chain, elongation and overall tensile deformation. And said inner portion 156, from said sealing-lip 134 to said section 155, the change of shape is shown, as the comprehensive effect of partial bending deformation and overall tensile deformation of the seal membrane. What it is quite clear is that said Concave-channels enlarge hoop circumference, and reduce the cylinder hoop strain (stress when a large diameter instrument is inserted, thereby reducing the hoop force and the frictional resistance.

Figure 14:
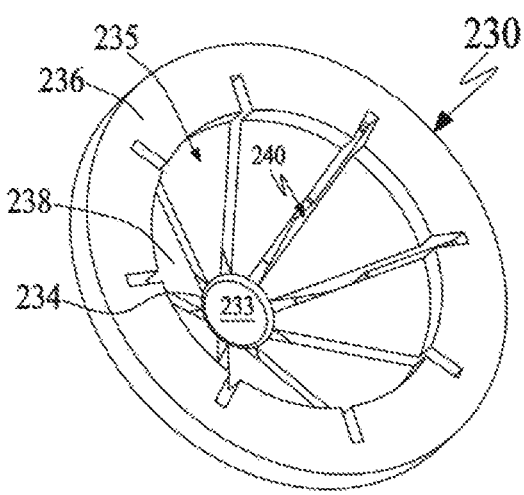
FIG. 14: shows a 3D perspective view of the seal membrane in the second embodiment.
Figure 15:
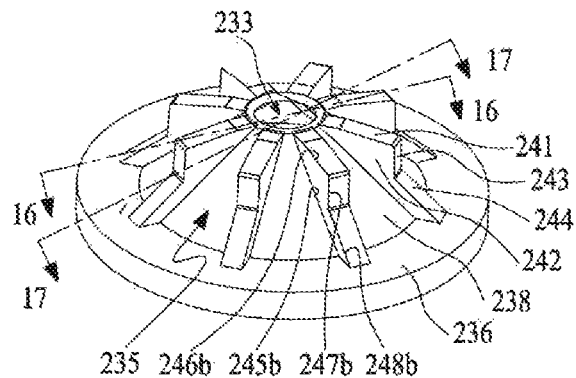
FIG. 15: shows, a 3D perspective reserve view of the seal membrane in FIG. 14.
Figure 16:
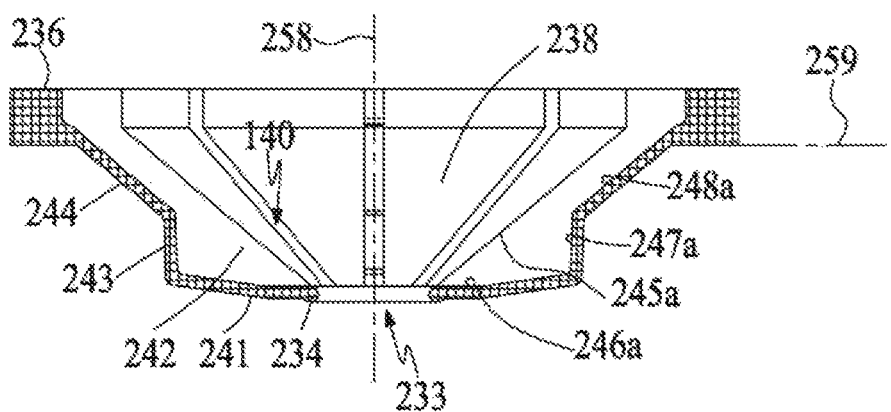
FIG. 16: shows a sectional view along line 16-16 in FIG. 15.
Figure 17:
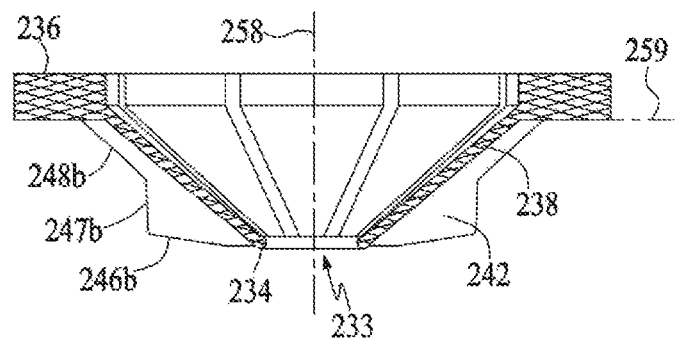
FIG. 17: shows a sectional view along line 17-17 in FIG. 15.
Figure 18:
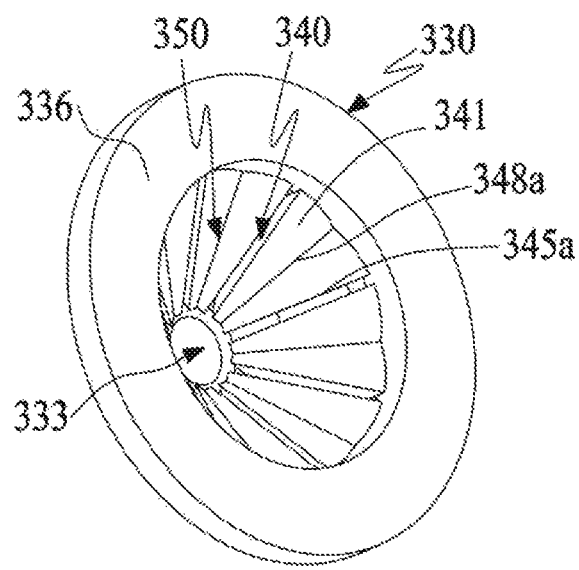
FIG. 18: shows a 3D perspective view of the seal membrane in the third embodiment.
Figure 19:
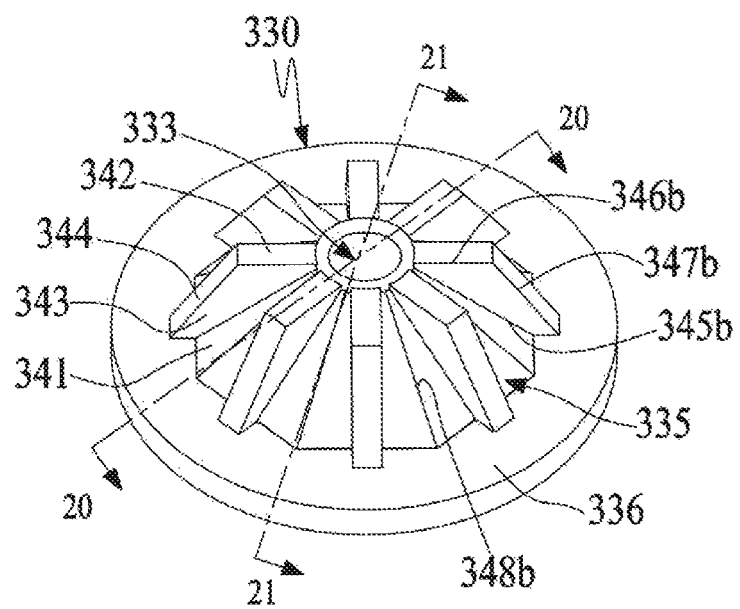
FIG. 19: shows a 3D perspective reserve view of the seal membrane in FIG. 18.
Figure 20:
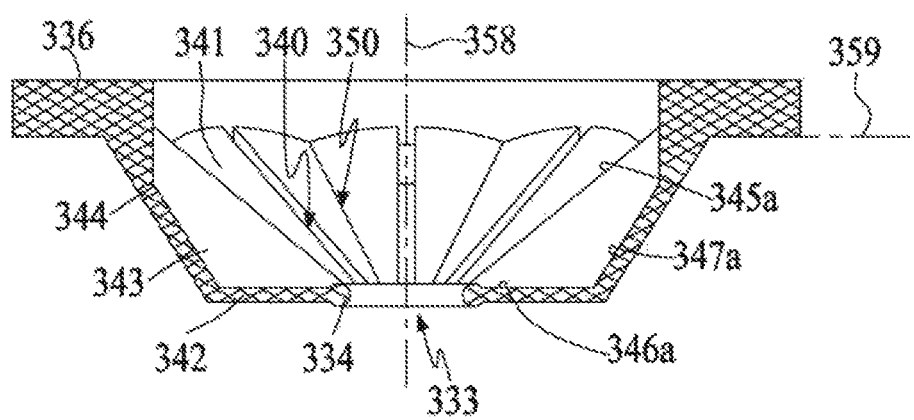
FIG. 20: shows a sectional view along line 20-20 in FIG. 19.
Figure 21:
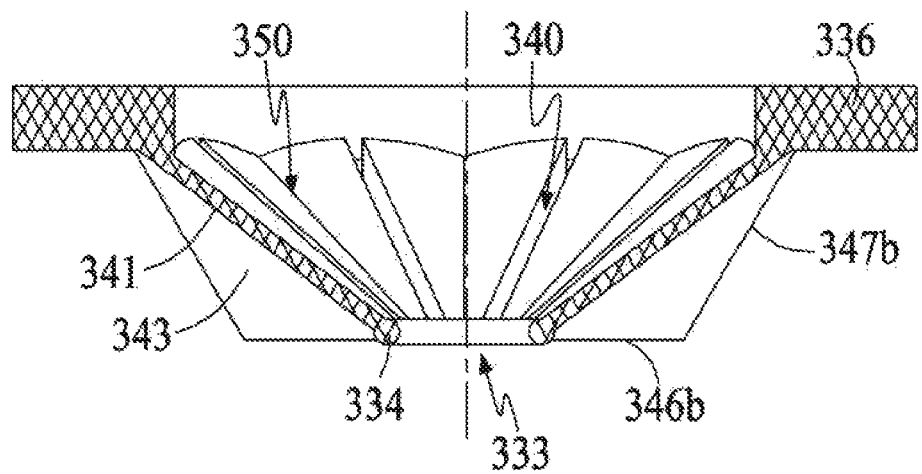
FIG. 21: shows a sectional view along line 21-21 in FIG. 19.

The Concave-channel 140 can be used to store grease. As FIG. 14-15 have shown, when a large diameter instrument is inserted, the wrapped area deformed by said Concave-channel is smaller, only a small section of the Concave-channel 140 is flattened. The unflattened Concave-channel near the wrapped area has a better function of storing grease. When the instrument moves in the seal membrane, the grease in the wrapped area is scraped away firstly, and the grease in the unflattened Concave-channel adjacent to the wrapped area will be added to the surface of the instrument, thereby adding to the wrapped area with the instrument moving. Optionally, the internal width of the Concave-channel in the lip-adjacent, area is B1, wherein 0.5 mm<B1<1 mm. When the inner width of the Concave-channel in the lip-adjacent area is smaller than 0.5 mm, the structure of the Concave-channel is hard to be manufactured; while the larger the internal width of the Concave-channel, the worse the grease storage effect; Researches have shown that when the internal width of the groove is ≤1 mm, the grease storage effect is better. The grease storage of the grooves improves the problem of lubrication unreliability as described in the background, thereby contributing to reduce the stick-slip described in the background.

Said side sealing-wall 142 has effects on reinforcing ribs similar to those described, in the background, all of the side sealing-walls 142 together reinforcing the axial tensile stiffness in the lip-adjacent area; and said side sealing-walls 142 increase the axial tensile stiffness without increasing the hoop stiffness, thus increasing the axial stiffness without increasing the hoop force, such that which can effectively reduce the stick-slip described in the background. In this embodiment, 16 side sealing-walls 142 are included, while more or less side sealing-walls also can increase the axial tensile stiffness.

In summary, the structure of Concave-channels has the functions of enlarging hoop circumference, reducing the wrapped area, reducing the actual contact area of the two surfaces, between the instrument and the seal membrane, improving lubrication reliability, increasing the axial tensile stiffness, etc., thereby, the frictional resistance and the stick-slip can be greatly reduced, and the probability of inversion is reduced and the comfort of application is improved.

The stress in the lip-adjacent area, especially said wrapped area, is highly concentrated when a large diameter instrument is inserted. It is easy to understand for those skilled in the art that the closer to the sealing-lip, the greater the cylinder strain (stress). It has been stated above that the method of increasing the hoop circumference cannot be used to reduce the cylinder strain (stress) of the sealing-lip, but the cylinder strain (stress) can be reduced by increasing the hoop circumference in the lip-adjacent area: Moreover, it is necessary to rapidly increase the hoop circumference in the lip-adjacent area so the cylinder strain (stress) in the lip-adjacent area is rapidly reduced to approximate zero. It has been stated above that said side scaling-wall 142 an important role to enlarge hoop circumference, when said side sealing-wall 142 extending laterally from the sealing-lip, the faster the rate of its width increased, the faster the rate of the hoop circumference enlarged in the lip-adjacent area, that is to say, the larger said angle θ is, the faster the rate of the hoop circumference enlarged in the lip-adjacent area.

Optionally, the geometry of said Concave-channel 140 is designed to conform to the following equation:

$$\theta \geq \arctan \frac{9\pi R(R_i - R)\cos\alpha}{P(R_i + 9R)(R - R_0)}$$

Where:
θ=angel between two edges of the concave-channel side sealing-wall in the lip-adjacent area;
α=the angle between the generating line of the main rotary-wall and the transverse plane surface in the lip-adjacent area (guide angle)
arctan=arctangent function:
cos=cosine function;
π=circumference ratio;
R=radius;
$R_i$=the largest radius designed for the surgical instrument passed through the seal membrane:
$R_0$=radius of the sealing-lip;
P=number of concave-channel.

An reasonable value of θ make the hoop circumference increased rapidly in the lip-adjacent area. According to the above equation, normally, Ri and R0 is constant; The variables α, P and R together affect the rate of hoop circumference enlarged. Normally selecting 0°≤α≤50°, by theoretical analysis and related research, it is shown that reducing the value of the guiding angle α is advantageous for reducing the length of said wrapped area. However, too small a guide angle α will sacrifice the guiding performance of the seal membrane, so it is necessary to base on the premise of satisfying the guiding performance when determining the value of a as small as possible. Normally 2.5 mm≤R≤(Ri+R0)/2. If the value of R is less than 2.5 mm, the transition area at the sealing-lip will be too large; if the value of R is geater than (Ri+R0)/2, the effect of enlarging the hoop circumference in the lip-adjacent area, and reducing the hoop force is not obvious. Reasonable values of α, P and R can ensure good guiding and minimize the wrapped area when a large diameter instrument is inserted, and the hoop force in the lip-adjacent area is rapidly reduced to a small value, or disappeared. It has been found that R=3.5, P=8, α=35° can ensure good guiding, and reduce the wrapped area and the hoop force. Approximate or possibly more efficient combinations of parameters can be obtained by theoretical calculations and simple experimental verification.

The design of said Concave-channel, as long as it conforms to the essence of the above equation, should be considered as be substantially coincident with the above equation. For instance, those skilled in the art readily conceive that said main rotary-wall 138, said inner measuring wall 141 or said side sealing-wall 142 is designed as non-linear curved surface; or deliberately designing the main rotary-wall 138, the inner wall 141 or the side sealing-wall 142 into a complex multi-faceted surface; the intersection line may not be a straight line, as long as the two intersection lines are viewed as a whole, the angle between the adjacent area of the sealing-lip substantially will conforms with the above equation, it can be considered that the scope of the present invention is not deviated.

The previous part has been described in detail the lip-adjacent area as an area with high concentration of stress, said strain (stress) outside, herein relatively small. As long as said Concave-channel in the lip-adjacent area substantially conforms to above equation, it is not necessary if the Concave-channel outside the lip-adjacent area conforms to the above equation or not. In this example, outside the lip-adjacent area, said side sealing-wall 142 is a surface defined by two sides extending laterally outward and gradually narrowing; that is, the depth of the Concave-channel 140 is, rapidly decreased outside the lip-adjacent area, which does not conform to the above equation. Those skilled in, the art will understand that such design of Concave-channel not only ensure that the Concave-channel has the functions of enlarging the hoop circumference, reducing the wrapped area and the two surfaces in contact between the instrument and the seal membrane, and increasing the axial tensile stiffness, etc., but also greatly simplify mold design, improve the efficiency of the seal membrane processing, and reducing the space occupied by the lateral movement of the sealing assembly, so that the size of trocar can be designed to be smaller.

FIG. 14-17 illustrate the second embodiment of the seal membrane 230 in the invention. Said seal membrane 230 includes a distal aperture 233, a sealing-lip 234, a sealing wall 235 and a flange 236, said distal aperture 233 formed by the sealing-lip 234, said sealing, wall 235 connecting the sealing-lip 234 at one end and the flange 236 at the other end, said the seal membrane 230 including the proximal surface and the distal surface, defining the axis of the sealing-lip 234 as the longitude axis 258, and defining the plane which is perpendicular to the longitude axis 258 as the transverse plane 259.

Said sealing wall 235 includes the main rotary-wall 238 and a plurality of Concave-channels 240. Said Concave-channels 240 extend laterally from the sealing-lip 234, in the lip-adjacent area, the depth of said Concave-channels 240 gradually increase along the axial direction of the sealing-lip, the opening of said Concave-channels 240 oriented to the proximal surface. In the lip-adjacent area, said a plurality of Concave-channels 240 are divided the main rotary-wall 238 approximately into a plurality of portions. That is, the sealing wall 235 is a seamless sealing wall formed by the main rotary-wall 238 and a plurality of Concave-channels 240 arranged around the sealing-lip 234 in an approximately conical manner. The sealing wall 235, in the present embodiment, comprises 8 linear concave-channels, however, a more or less number of non-linear Concave-channels may be adopted. The section of the concave-channel, is approximately U-shaped.

Said Concave-channel includes a lower sealing-wall 241, a side sealing-wall 242, the first-tilted sealing-wall 243 and the second-tilted sealing-wall 244. The first edge of said side sealing-wall 242 and said main rotary-wall 238 formed an intersection line 245a, 245b; the second edge of said side sealing-wall 242 and said lower sealing-wall 241 formed an intersection line 246a, 246b; the third edge of said side sealing-wall 242 and said first-tilted sealing-wall 243 formed an intersection line 247a, 247b; the forth edge of said side sealing-wall 242 and said second-tilted sealing-wall 244 formed an intersection line 248a, 248b; Said lower sealing-wall 241, said first-tilted sealing-wall 243 and second-tilted sealing-wall 244 are together formed an approximately ladder-shape. Defining the angle between said intersection line 245a (245b) and said transverse plane surface 159 as $\alpha$, which is called the guide angle, and $0 \le \kappa < 90$; The angle between said intersection line 245b and said intersection line 246b (or between said intersection line 245a and said intersection line 246a) is defined as $\gamma$. The intersection of the two intersection lines (i.e. the apex of the angle $\gamma$) may be on the sealing-lip 234; or the virtual, extension lines of the two intersection lines intersect the inside of the sealing-lip 234.

In the lip-adjacent area, the side sealing-wall 242 is a surface defined by both edges and extending laterally outward from the sealing-lip 134 and gradually widening. While far away the lip-adjacent area, the width of the side sealing-wall 242 is rapidly reduced first, and then extending to the flange in the case of maintaining a constant width. When the Concave-channels 240 extending laterally outward, the depth of said Concave-channels increase along longitudinal axis of the sealing-lip and then rapidly decreases to a certain depth, and then extending laterally outward to the flange in the case of maintaining a constant width, that is, the Concave-channels 240 are ladder-shaped. In the lip-adjacent area, said Concave-channels 240 is substantially identical to said Concave-channels 140; the only difference lies outside the lip-adjacent area. Said, ladder-shape is conducive to reduce overall diastolic deformation outside the lip-adjacent area, when the large diameter instrument is inserted. Since the ladder-shaped Concave-channels 240 has a ladder-shaped side surface 243, the axial tensile stiffness of the sealing wall 235 can be enhanced to reduce stick-slip. Meanwhile, when the seal membrane is inverted, the ladder-shaped Concave-channels 240 has a significant effect of reducing the actual contact area between the instrument and the seal membrane. Similarly, said Concave-channels 240 is provided with other related advantages of the Concave-channels 140. Alternatively, the angle $\gamma$ and the guiding angle $\kappa$ also approximate the aforementioned equation of $\theta$ angle, so the Concave-channels increase the hoop circumference faster. (i.e. $\gamma$ is substituted for $\theta$ in the aforementioned equation, and $\kappa$ is substituted for $\alpha$ in the aforementioned equation).

FIG. 18-21 illustrate the third embodiment of the seal membrane 330 of the present invention. Said seal membrane 330 includes a distal aperture 333, a sealing-lip 334, a sealing wall 335 and a flange 336, said distal aperture 333 formed by the sealing-lip 334, said sealing wall 335 connecting the scaling-lip 334 at one end and the flange 336 at the other end. Said the seal membrane 330 includes the proximal surface and the distal surface, defining the axis of the sealing-lip 334 as the longitude axis 358, and defining the plane which is perpendicular to the longitude axis 358 as the transverse plane 359.

Said sealing wall includes the inner side sealing-wall 341, the outer side sealing-wall 342, the side sealing-wall 343 and a tilted sealing-wall 344. Said inner side sealing-wall 341 extends laterally from the sealing-lip 334 to said flange 336; said outer side sealing-wall 342 extends laterally, from the sealing-lip 334 to said tilted sealing-wall 344 which extends to said flange 336. The first edge of said side sealing-wall 343 and said inner side sealing-wall 341 formed an intersection line 345a, 345b; the second edge of said side sealing-wall 343 and said outer side sealing-wall 342 formed an intersection line 346a, 346b; the third edge of said side sealing-wall 343 and said tilted sealing-wall 344 formed an intersection line 347a, 347b; the two adjacent side sealing-walls 341 formed an intersection line 348a, 348b.

In the adjacent area of the sealing-lip 334, the two adjacent side sealing-walls 343 and the outer side sealing-wall 342 there between intersect to form an approximately U-shaped Concave-channel the opening of which toward oriented to the distal surface, defined as U-shaped Concave-channels 340. The two adjacent side sealing-walls 341 are formed approximately V-shaped pleats the opening of which toward oriented to the distal surface, defined as V-shaped shaped 350.

Taking the longitudinal axis 358 as a rotary axis, make a cylindrical surface with a radius R2 and intersects with said inner side sealing-wall 341 to form an intersection line, and create cutting plane M2 through said intersection line and perpendicular to the generating line of said inner side sealing-wall 341 (with the axis 358 as rotary axis). Said cutting plane M2 divides the seal membrane 330 into an inner portion 356 (as in FIG. 22) and an outer portion 357 (FIG. 23). Said cutting plane M2 intersects said inner side sealing-wall 341 to form a plurality of intersection lines 351a and 351b. Said cutting plane M2 intersects the side sealing-wall 343 to form a plurality of intersection lines 353a and 353b, and said cutting plane M2 intersects said inner side sealing-wall 342 to form a plurality of intersection lines 352a and 352b. The plurality of segments 351a, 352a, 353a arc formed an annular intersection line 355a; the plurality of segments 351b, 352b, 353b are formed an annular intersection line 355b, and the section 355 defined by said annular intersection line 355a and 355b.

Figure 22:
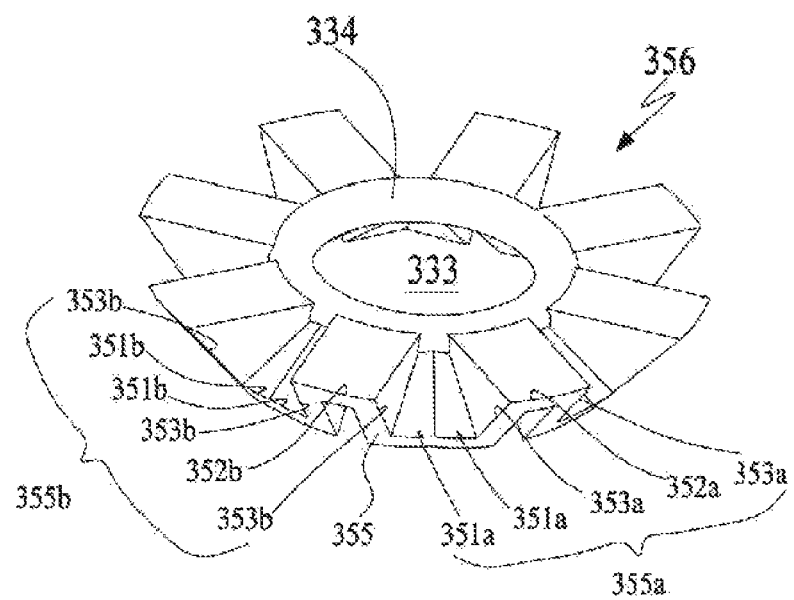
FIG. 22-23: shows a segmentation view of the seal membrane after the circumferential cutting separation in FIG. 19.
Figure 23:
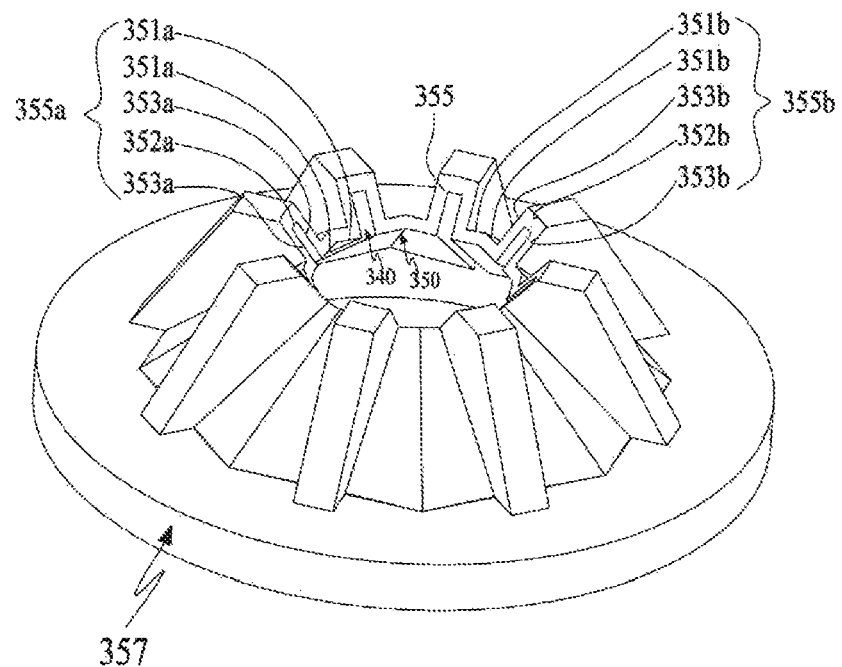
Figure 24:
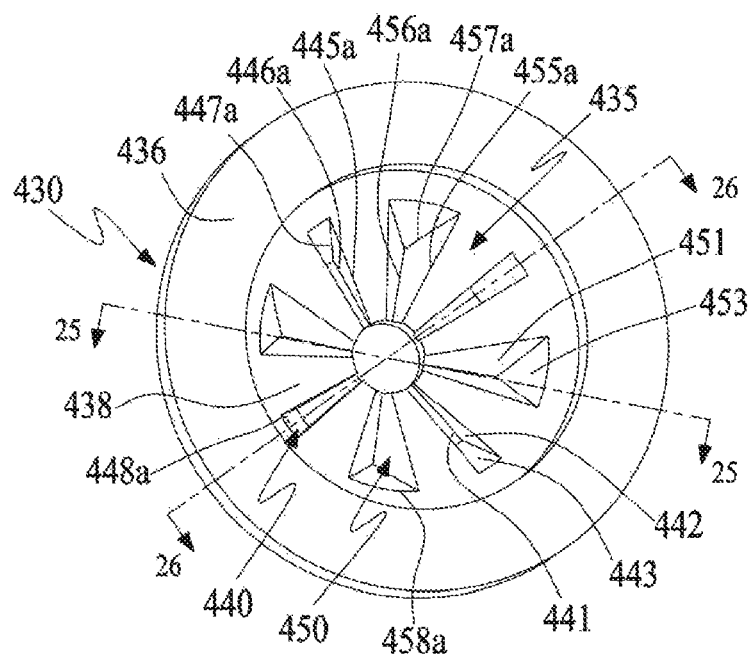
FIG. 24: shows a 3D perspective view of the seal membrane in the fourth embodiment.
Figure 25:
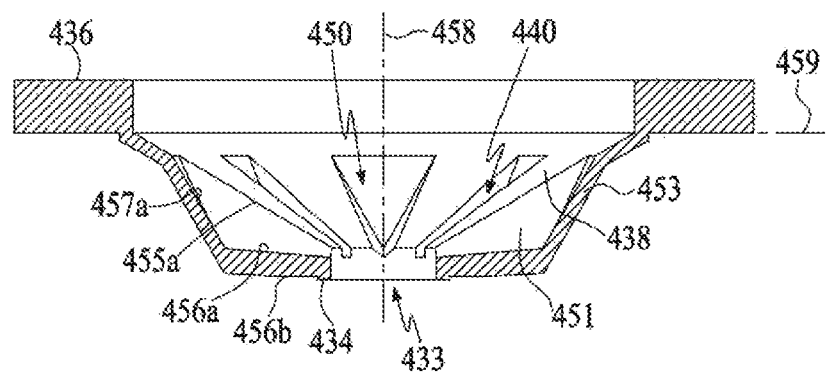
FIG. 25: shows a sectional view along line 25-25 in FIG. 24.
Figure 26:
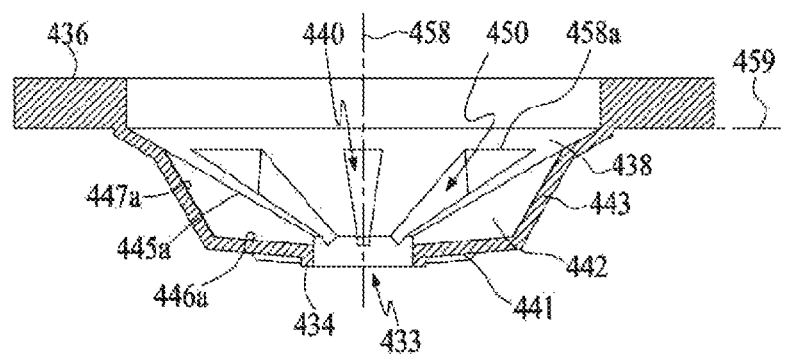
FIG. 26: shows a sectional view along line 26-26 in FIG. 24.
Figure 27:
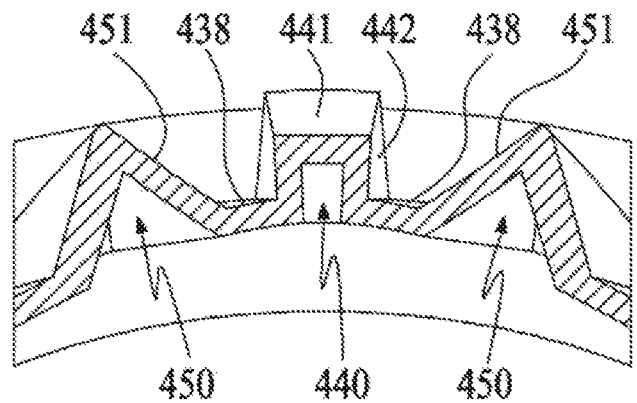
FIG. 27: shows a partial sectional view along line 27-27 in FIG. 28.

As shown in FIG. 22-23, it is obvious that the circumference L1 of the intersection line 355a (355b) is much larger than $2*\pi*R2$, that means the Concave-channel plays a role in enlarging hoop circumference. In the present embodiment, there are 8 U-shaped Concave-channels 340 and 8 V-shaped pleats. The side sealing-wall 343 of U-shaped Concave-channels 340 actually plays a role in enlarging hoop circumference. The V-shaped pleats 350 formed by the mutually intersected inner side sealing-walls 341 also have the effect of enlarging the hoop circumference of the sealing-lip; while the V-shaped pleats 350, relative to the Concave-channels 340, to enlarge the hoop circumference is negligible. The V-shaped pleats 350 mainly serve to reduce the actual contact area of the sealing-lip and increase the axial tensile stiffness of the seal membrane.

Those skilled in the art can understand that there must be some R1 value making the outer portion 3157, which is divided by the cutting plane M1, to start from the section 355, the main change of its shape is shown as local bending deformation and macroscopic displacement of the seal membrane, rather than the overall microscopic molecular chain elongation and overall tensile deformation. And said inner portion 356, from, said sealing-lip 334 to said section 355, the change of shape is shown as the comprehensive effect of partial bending deformation and overall tensile deformation of the seal membrane. What it is quite clear is that said Concave-channels enlarge hoop circumference, and reduce the cylinder hoop strain (stress) when a large diameter instrument is inserted, thereby reducing the hoop force and the frictional resistance.

It should be understood by those skilled in the art, theoretically, the lip-adjacent area may comprise numerous Concave-channels, however, in fact, due to the small hoop circumference of the sealing-lip, it is impossible to design too many Concave-channels around the sealing-lip; under the premise of the same dimension, that the U-shaped Concave-channels have a greater ability to increase the hoop circumference than the V-shaped Concave-channels. Normally, the thickness of the side sealing-wall 343 of the U-shaped Concave-channels is ≥0.4 mm, and the inner width of the Concave-channels 340 is ≥0.5 mm. The number of the U-shaped Concave-channels 340 in the seal membrane, is usually no more than eight. Too many of the U-shaped Concave-channels will result in difficulty in mold manufacturing or an increase in failure rate of production process. Although it is difficult to produce more Concave-channels, on the inner side sealing-wall 341 or the outer side sealing-wall 342, a shallow V-shaped pleats can be designed to reduce the actual contact area and increase the axial tensile stiffness when applying a large diameter instrument. In the present embodiment, the seal membrane 330 comprises 8 U-shaped Concave-channels 340 and 8 V-shaped pleats 350.

FIG. 24-28 show more detailed depiction the seal membrane 430 of the forth embodiment of the invention. Said seal membrane 430 includes a distal aperture 433, a sealing-lip 434, a sealing wall 435 and a flange 436. Said distal aperture 433 is formed by the sealing-lip 234, and said the sealing-lip 434 is cylindrical. Said sealing wall 435 connects the sealing-lip 434 at one end and the flange 436 at the other end, said the seal membrane 430 including the proximal surface and the distal surface, defining the axis of the sealing-lip 434 as the longitude axis 458, and defining; the plane which is perpendicular to the longitude axis 458 as the transverse plane 459.

Said sealing wall 435 includes U-shaped Concave-channels 440 and a plurality of V-shaped Concave-channels 450. The Concave-channels 440 and said Concave-channels 450 extend laterally from the sealing-lip 234, in the lip-adjacent area, the depth of said Concave-channels gradually increases along the axial direction of the sealing-lip, the opening of said Concave-channels oriented to the proximal surface. In the lip-adjacent area, said a plurality of Concave-channels are divided the main rotary-wall 438 approximately into a plurality of portions. That is, the sealing wall 435 is a seamless sealing wall formed by the main rotary-wall 438 and a plurality of Concave-channels arranged, around the sealing-lip 434 in an approximately conical manner. The sealing wall 435, in, the present embodiment, comprises 4 linear U-shaped Concave-channels and 4 linear V-shaped Concave-channels, however, a more or less number of non-linear Concave-channels may be adopted.

Said U-shaped Concave-channels 440 include a lower-sealing-wall 441, a side scaling-wall 442 and a tilted scaling-wall 443. The first edge of said side sealing-wall 442 and said the main rotary-wall 438 formed an intersection line 445a, 445b; the second edge of said side sealing-wall 442 and said lower sealing-wall 441 formed an intersection line 446a, 446b; the third edge of said side sealing-wall 442 and said tilted sealing-wall 443 formed an intersection line 447a, 447b; and said tilted sealing-wall 443 and said main rotary-wall 438 formed an intersection line 448a, 448b. Said V-shaped Concave-channels comprise a side sealing-wall 451 and a tilted sealing-wall 453, the two adjacent side sealing-walls 451 formed an, intersection line 455a, 455b, the other edge of said side sealing-wall 451 and said the main rotary-wall 438 formed an intersection line 456a, 456b; said side sealing-wall 451 and said tilted sealing-wall 453 formed an intersection line 457a, 457b, Said tilted sealing-wall 453 and said the main rotary-wall 438 formed an intersection line 458a, 458b; Although the tilted sealing-wall 443 and the tilted sealing-wall 453 are not parallel with said axis 458 in this embodiment, they can be parallel to said axis 458.

It could be understood by those skilled in the art, theoretically, the lip-adjacent area may comprise numerous Concave-channels, however, in fact, due to the small hoop circumference of the sealing-lip, it is impossible to design too many Concave-channels around the sealing-lip; under the premise of the same dimension, that the U-shaped Concave-channels have a greater ability to increase the hoop circumference than the V-shaped Concave-channels. Normally, the thickness, of the side sealing-wall 442 of the U-shaped Concave-channels is mm, and the inner width of said Concave-channels 440 is ≥0.5 mm. Too many of said U-shaped Concave-channels will result in difficulty in mold manufacturing or an, increase in failure rate of production process. However, said V-shaped Concave-channels are simpler and more economical to manufacture and more productive than said U-shaped Concave-channels. Therefore, it is possible to adopt a seal membrane comprising both U-shaped Concave-channels and a V-shaped Concave-channel, thereby obtaining the seal membrane excellent in functional performance and more economical in cost. The seal membrane 430, in the present embodiment, comprises 4 linear U-shaped Concave-channels and 4 linear V-shaped Concave-channels, however, a more or less number of non-linear Concave-channels may be adopted. Said U-shaped Concave-channels and V-shaped Concave-channels are arranged alternately, however, a smaller number of U-shaped and V-shaped Concave-channels may be adopted; or U-shaped and V-shaped Concave-channels freely combined; or all V-shaped Concave-channels adopted. The seal membrane 430 also has the functions of enlarging hoop circumference, reducing the wrapped area, reducing the actual contact area of the two surfaces between the instrument and the seal membrane, improving lubrication reliability, increasing the axial tensile stiffness, etc., thereby, the frictional resistance and the stick-slip can be greatly reduced, and the probability of inversion, is reduced and the comfort of application is improved.

Figure 28:
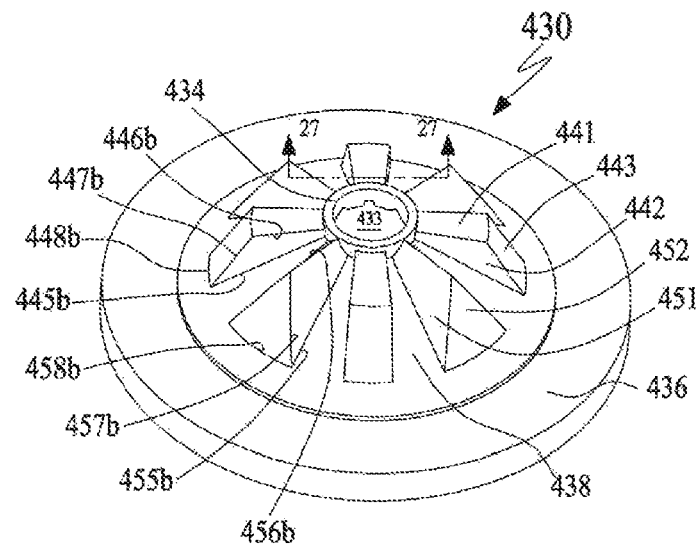
FIG. 28: shows, a 3D perspective reserve view of the seal membrane in FIG. 24.
Figure 29:
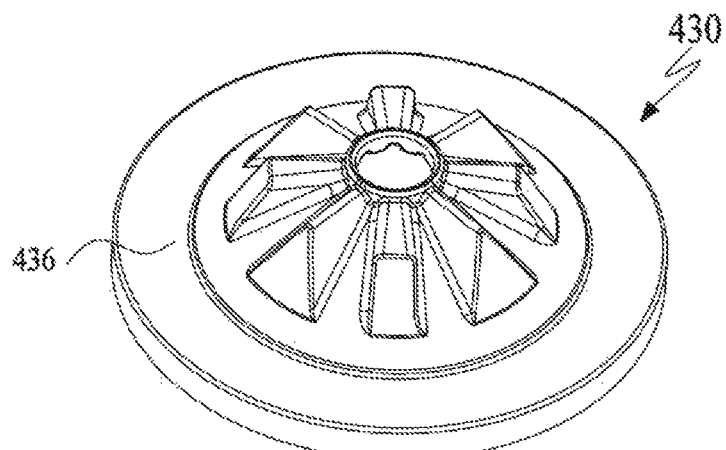
FIG. 29: shows a same 3D perspective view of the seal membrane after fillet in FIG. 28.

Those skilled in the art easily understand that the reasonable fillet transition can avoid stress concentration or make certain areas deformed more easily. Due to the small size of the seal membrane, especially the area near the sealing-lip is smaller, with such a small size and different chamfer, the shape of the seal membrane looks different. For example, FIG. 28 shows, a 3D perspective reserve view of the seal membrane before fillet, while FIG. 29 shows a same 3D perspective view of the seal membrane after fillet in FIG. 28. It is apparent that FIG. 28 more clearly expresses the relationship between the various geometric elements comprised the sealing body 430. In order to clearly show the geometric relationship of the elements, the embodiment of the invention is generally the pattern without the fillet.

Many different embodiments and examples of the invention have been shown and described. One of those, ordinary skilled in the art will be able to make adaptations to the methods and apparatus by appropriate modifications without departing from the scope of the invention. The structure and the fixing manner of the protector assembly disclosed in U.S. Pat. No. 7,788,861 are used in the example of the present invention. While the structure and the fixing manner of the protector assembly disclosed in U.S. Pat. No. 5,342,315, 7,988,671, or US 20050131349A1 can be used; or simply modify the fixing manner of the protector; in some applications, the protector assembly may not be included. For example, the approximate U-shaped Concave-channels and the approximate V-shaped Concave-channels described in this embodiment cannot be limited to U-shaped or V-shaped. It has been mentioned many times in the invention that the Concave-channel extends laterally outward from the sealing-lip, and the so-called "extending laterally outward" should not be limited to a straight line. Said "extending laterally outward" can be a spiral, a line segment, a multi-section arc line and so on. In the invention, the positional relationship of the intersecting surfaces composed of said Concave-channel and the intersection line thereof are described with reference to specific embodiments, and the methods of increasing curved surfaces to form a multifaceted mosaic or using of the high-order curved surface to make the intersection line and the Concave-channel shape to look different from said embodiment. However, it can be considered not deviated from the scope of the invention, as long as it conforms to the general idea of the invention. Several modifications have been mentioned, to those skilled in the art, other modifications are also conceivable. Therefore, the scope of the invention should follow the additional claims, and at the same time, it should not be understood that it is limited by the specification of the structure, material or behavior illustrated and documented in the description and drawings.

I claim:

1. A trocar seal membrane for minimally invasive surgery, comprising:
    a proximal opening, a distal aperture and a sealing wall extending from the distal aperture to the proximal opening; the sealing wall comprising a proximal surface and a distal surface, the distal aperture formed by a sealing-lip for accommodating an inserted instrument;
    the sealing wall comprising a main rotary-wall and a plurality of concave-channels; each concave-channel comprising two side sealing-walls, and the side sealing-walls limited by two edges extending laterally outward from the sealing lip and having a gradually increasing width;
    the concave-channels recessed from the proximal surface of the main rotary-wall toward the distal surface and dividing the main rotary-wall into multiple areas, and
    the side sealing-wall extending laterally outward from the sealing-lip and widening in width along longitudinal axis of the sealing-lip within an area adjacent to the lip; while
    the side sealing-wall having a width firstly reducing outward to a constant value from the area adjacent to the lip, and then extending laterally outward with the width maintaining the constant value; and the concave-channels are ladder-shaped.

2. The seal membrane according to claim 1, wherein a thickness of the main rotary-wall and a thickness of the side sealing-walls are substantially uniform.

3. The seal membrane according to claim 2, wherein the main rotary-wall is frustum-shaped.

4. The seal membrane according to claim 2, wherein the seal membrane comprises a flange which extends to intersect with the main rotary-wall or simultaneously intersect with the main rotary-wall and the concave-channels.

5. The seal membrane according to claim 4, wherein the seal membrane comprises an outer floating portion with at least one lateral pleat extending from the flange to the proximal opening.

6. A trocar comprising a seal assembly, the seal assembly comprising the seal membrane according to claim 5 and a lower retainer ring, an upper retainer ring, a protection device, an upper body and an upper cover; the seal membrane and the protection device are sandwiched between the upper retainer ring and the lower retainer ring, the proximal opening is sandwiched between the upper body and the upper cover.

7. The seal membrane according to claim 1, wherein the concave-channels divide the main rotary-wall into multiple areas, and the main rotary-wall comprising a plurality of V-shaped pleats.

8. The seal membrane according to claim 7, the sealing wall comprises 8 V-shaped pleats and 8 concave-channels arranged alternately.

9. The seal membrane according to claim 1, the concave-channels recessed from the proximal surface of the main rotary-wall toward the distal surface and divide the main rotary-wall into multiple areas, and the concave-channels comprising a plurality of concave-channels and a plurality of V-shaped concave-channels; and the concave-channel and the V-shaped concave-channel are alternately distributed around the sealing-lip in an approximately conical manner.

* * * * *